United States Patent
Ziv-Ari et al.

(10) Patent No.: US 9,513,368 B2
(45) Date of Patent: Dec. 6, 2016

(54) METHOD AND SYSTEM FOR ULTRASOUND DATA PROCESSING

(75) Inventors: Morris Ziv-Ari, Atlit (IL); Arcady Kempinski, Haifa (IL); Alexander Sokulin, Kiryat Tivon (IL)

(73) Assignee: General Electric Company, Schenectady, NY (US)

(*) Notice: Subject to any disclaimer, the term of this patent is extended or adjusted under 35 U.S.C. 154(b) by 1272 days.

(21) Appl. No.: 12/827,314

(22) Filed: Jun. 30, 2010

(65) Prior Publication Data

US 2012/0004545 A1 Jan. 5, 2012

(51) Int. Cl.
| | |
|---|---|
| G01S 7/52 | (2006.01) |
| G01S 15/89 | (2006.01) |
| A61B 8/08 | (2006.01) |
| A61B 8/14 | (2006.01) |
| A61B 8/00 | (2006.01) |

(52) U.S. Cl.
CPC ......... G01S 7/52046 (2013.01); A61B 8/5207 (2013.01); G01S 7/52082 (2013.01); G01S 7/52084 (2013.01); G01S 15/8906 (2013.01); A61B 8/0883 (2013.01); A61B 8/14 (2013.01); A61B 8/4405 (2013.01); A61B 8/483 (2013.01);

(Continued)

(58) Field of Classification Search
CPC ....... A61B 8/0883; A61B 8/14; A61B 8/4405; A61B 8/483; A61B 8/486; A61B 8/488; A61B 8/5207; G01S 15/8906; G01S 7/52046; G01S 7/52082; G01S 7/52084; G01S 7/52095
USPC .................. 600/437, 443; 382/128
See application file for complete search history.

(56) References Cited

U.S. PATENT DOCUMENTS

| | | | | |
|---|---|---|---|---|
| 5,718,230 A | * | 2/1998 | Chapman et al. | 600/453 |
| 6,001,062 A | * | 12/1999 | Masters | 600/443 |

(Continued)

FOREIGN PATENT DOCUMENTS

| | | |
|---|---|---|
| CN | 101249002 A | 8/2008 |
| JP | 07116162 | 5/1996 |

(Continued)

OTHER PUBLICATIONS

Ivan K.H. Tsang, et al., Design of a Multi-Channel Pre-Beamform Data Acquisition System for an Ultrasound Research Scanner, Medical Engineering Program, The University of Hong Kong, Pokfulam, Hong Kong SAR, Ultrasonix Medical Corporation, Richmond, BC, Canada, Corresponding Emails: alfred.yu@hku.hk, ivan_tsang@hku.hk, (4) pgs.

(Continued)

*Primary Examiner* — Katherine Fernandez
(74) *Attorney, Agent, or Firm* — Dean D. Small; The Small Patent Law Group, LLC.

(57) ABSTRACT

Methods and systems for ultrasound data processing are provided. One method includes acquiring channel ultrasound data from a plurality of channel connected to a plurality of elements of an ultrasound probe and storing the channel ultrasound data from the plurality of channels. The method further includes generating ultrasound images based on processing of the acquired channel ultrasound data and displaying the ultrasound images. The method also includes performing additional processing on the stored channel ultrasound data while the ultrasound images are displayed and displaying updated ultrasound images generated by the additional processing.

14 Claims, 10 Drawing Sheets

(52) U.S. Cl.
    CPC ............... *A61B 8/486* (2013.01); *A61B 8/488* (2013.01); *G01S 7/52095* (2013.01)

(56) References Cited

U.S. PATENT DOCUMENTS

| | | | |
|---|---|---|---|
| 6,083,168 A * | 7/2000 | Hossack et al. | 600/443 |
| 6,086,537 A * | 7/2000 | Urbano et al. | 600/443 |
| 6,123,670 A * | 9/2000 | Mo | 600/447 |
| 6,482,160 B1 * | 11/2002 | Stergiopoulos et al. | 600/443 |
| 6,947,584 B1 * | 9/2005 | Avila et al. | 382/131 |
| 7,402,136 B2 * | 7/2008 | Hossack et al. | 600/447 |
| 8,784,318 B1 * | 7/2014 | Napolitano et al. | 600/443 |
| 2004/0006271 A1 * | 1/2004 | Golland et al. | 600/443 |
| 2007/0239001 A1 * | 10/2007 | Mehi et al. | 600/437 |
| 2008/0205715 A1 | 8/2008 | Halmann | |

FOREIGN PATENT DOCUMENTS

| | | |
|---|---|---|
| JP | 2002306479 | 10/2002 |
| WO | WO2009158399 | 12/2009 |

OTHER PUBLICATIONS

Unofficial translation of CN Office Action from CN Application No. 201010623685.7 dated Apr. 1, 2013.
Unofficial translation of CN Search Report from CN Application No. 201010623685.7 dated Apr. 1, 2013.
English translation of Abstract for JP2002306479.
English translation of Abstract for JP07116162.

* cited by examiner

METHOD AND SYSTEM FOR ULTRASOUND DATA PROCESSING

BACKGROUND OF THE INVENTION

The subject matter disclosed herein relates generally to ultrasound systems, and more particularly to systems and methods for processing received data in the ultrasound systems to form images.

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound probes typically include an array or matrix of transmit/receive elements, which transmit ultrasound waves and receive back-scattered echo signals. The ultrasound systems are controllable to operate in different modes of operation and to perform different scans. The received signals are then processed to form images for display to a user.

In ultrasound systems, the processing power or capabilities of the beamformer limits the beamforming techniques that can be used. In particular, some beamforming techniques can be complex or processor intensive. Thus, in some instances or applications, the beamforming can take longer than the acquisition time, such that real-time viewing of beamformed data is not possible. Moreover, images may not be displayed while storing the beamformed data because of the processing limitations. Additionally, if different beamforming techniques are to be used, multiple scans are needed. These multiple scans are needed because as the ultrasound signals are acquired during a particular scan, one type of beamforming is performed, which prevents subsequent beamforming from being performed on that acquired data.

Thus, image or volume frame rates and image quality of conventional ultrasound systems are limited by the beamformer processing power and the efficiency of the beamforming technique used.

BRIEF DESCRIPTION OF THE INVENTION

In accordance with various embodiments, a method for forming images from ultrasound data is provided. The method includes acquiring channel ultrasound data from a plurality of channel connected to a plurality of elements of an ultrasound probe and storing the channel ultrasound data from the plurality of channels. The method further includes generating ultrasound images based on processing of the acquired channel ultrasound data and displaying the ultrasound images. The method also includes performing additional processing on the stored channel ultrasound data while the ultrasound images are displayed and displaying updated ultrasound images generated by the additional processing.

In accordance with other various embodiments, a method for beamforming in an ultrasound system is provided. The method includes performing ultrasound beamforming during data acquisition based on a real-time processing capability of the ultrasound system and performing additional beamforming during image replay to increase image quality above an image quality level for the real-time processing capability.

In accordance with yet other various embodiments, an ultrasound system is provided that includes an ultrasound probe for acquiring channel ultrasound data for an object of interest and a memory for storing the channel ultrasound data acquired by the ultrasound probe. The ultrasound system further includes a display for displaying ultrasound images and a software beamformer configured to beamform the channel ultrasound data to form images for display on the display and to further beamform the channel ultrasound data while the ultrasound images are being displayed to form updated images.

In accordance with still other various embodiments, a method for forming images from ultrasound data is provided. The method includes acquiring channel ultrasound data from a plurality of channel connected to a plurality of elements of an ultrasound probe and storing the channel ultrasound data from the plurality of channels. The method further includes forming a pixel image directly from the stored channel ultrasound data without creating beams and displaying the pixel image. The method also includes performing additional processing on the acquired channel ultrasound data while the pixel image is displayed and displaying an updated ultrasound image formed by the additional processing.

DETAILED DESCRIPTION OF THE INVENTION

Figure 1:
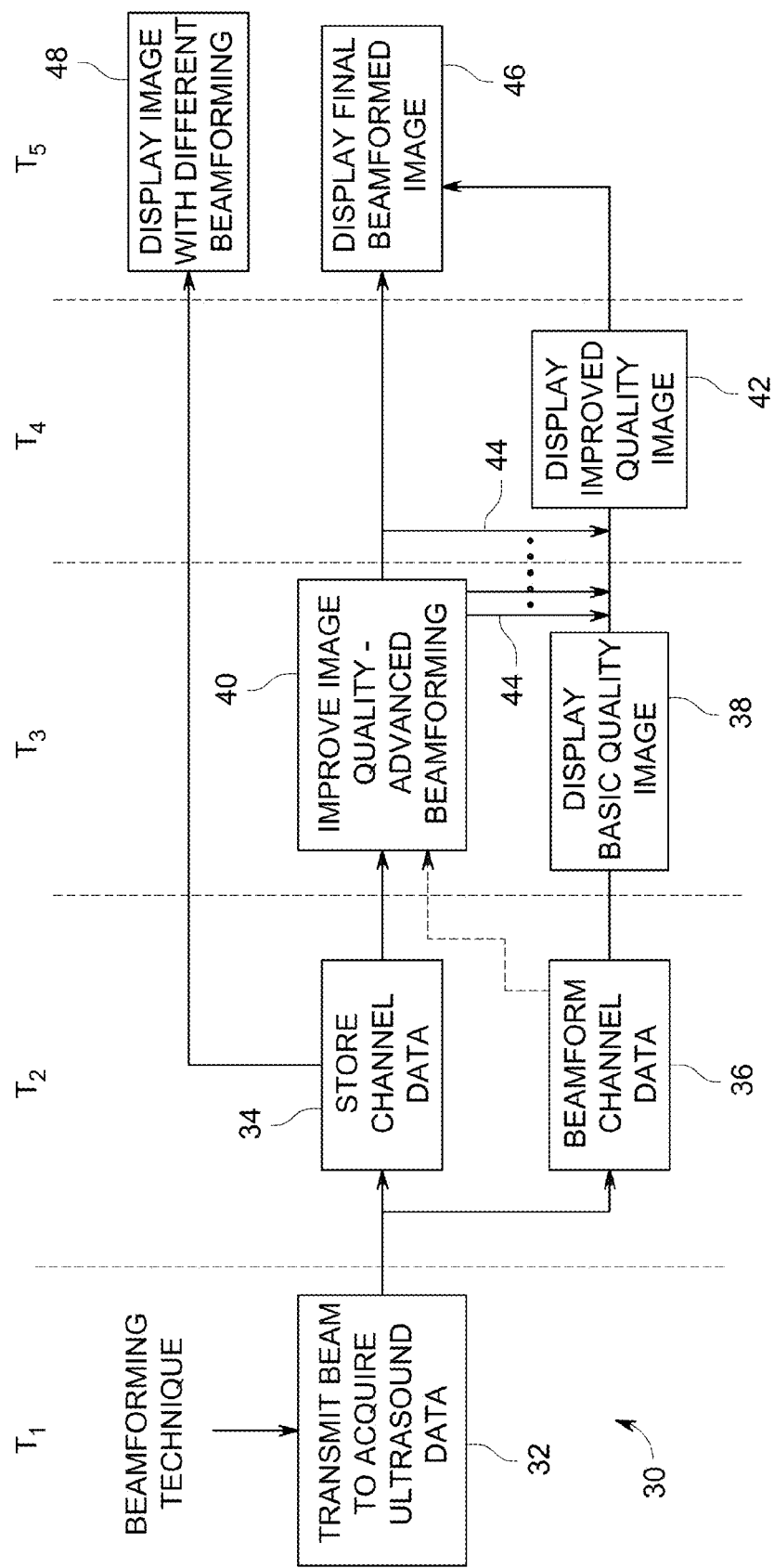
FIG. 1 is a block diagram illustrating a beamforming process performed in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a system and method for ultrasound data processing, such as beamforming, in particular, receive beamforming to generate images. By practicing some embodiments, processing (e.g., beamforming) is performed completely or partially during a live scanning mode, for example, during a scanning session, which may also include image replay(s) or image freeze(s). A technical effect of at least one embodiment is providing improved image quality using processing, such as beamforming that otherwise could not be performed using an ultrasound system based on the processing power or capabilities of that system. Another technical effect of at least one embodiment includes performing higher frame rate ultrasound imaging with increased image quality using ultrasound systems having lower processing power or capabilities.

In accordance with various embodiments, a process 30 for forming images from ultrasound data is illustrated by the system workflow diagram of FIG. 1. The process 30 may be implemented to generate or form ultrasound images using different types of channel data processing. It should be noted that although the process 30 is described in connection with beamform processing, the process 30 and the embodiments described herein are not limited to beamform processing, but may be implemented to form images using different processing techniques and methods, such as to form pixel images directly from channel data without creating beams. In general, the various embodiments may process stored data to improve the quality of images to be displayed while lower quality images are being displayed. Thus, in the various embodiments and as illustrated in some of the Figures, when reference is made herein to beamforming, additional or different processing methods are contemplated and may be implemented in the same or similar manner, such as using the same or similar system workflow.

It should be noted that the various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event.

In various embodiments, the processing to form images may include, for example, for each desired image reconstruction point, generating a general linear combination of time delayed and/or phase shifted channel data, where the channel data may originate from the same or different ultrasound transmit events, and where the time delay/phase shifting is selected to focus the image at or close to the image reconstruction point. The set of image reconstruction points also may include scan lines (vectors), pixels of the display or other suitable geometries.

The process 30 generally includes storing channel ultrasound data (e.g., raw channel data) for processing both during image data acquisition with the ultrasound system and thereafter using one or more different beamforming techniques. It should be noted that when reference is made herein to beamforming techniques, this generally refers to any type of receive beamforming that may be performed by the ultrasound system. The process 30 also may utilize software beamforming, hardware beamforming, or a combination thereof.

The process 30 illustrates an embodiment of a beamforming processing workflow in time (shown during a time period $T_1$ to $T_5$). In particular, at time period $T_1$, the ultrasound system transmits beams (using a probe of the ultrasound system) at 32 to acquire ultrasound data (e.g., channel or raw data) from an object, for example, a region of interest (ROI) of a patient. The transmit beams are formed based on desired or required image data to be acquired. For example, based on a selected or predetermined (based on an operating mode) receive beamforming technique, the transmit beams are formed using a transmit beamforming process. The transmit beamforming may be any suitable type of transmit beamforming that allows for the acquisition of ultrasound image data, such as, for generating certain types of ultrasound images.

Figure 2:
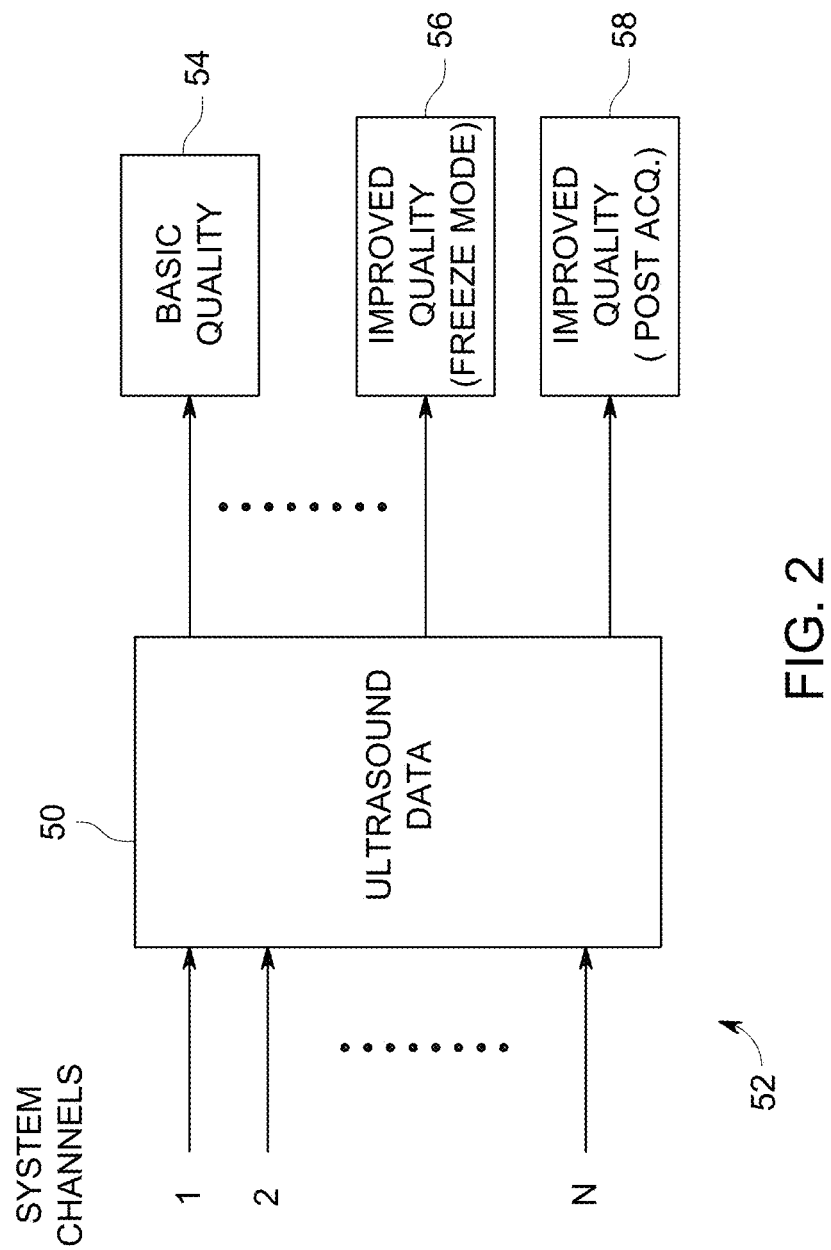
FIG. 2 is a block diagram illustrating different images generated by a beamforming process in accordance with various embodiments.

Thereafter, at time period $T_2$, the channel ultrasound data is stored at 34. For example, ultrasound data from each of a plurality of channels 52 of an ultrasound system are stored in a system memory 50 as illustrated in FIG. 2. Thus, channel ultrasound data is stored per channel 52 for each transmit signal. For example, in a 128 channel ultrasound system, a set of 128 receive signals are stored in the memory 50. Accordingly, this channel ultrasound data is stored prior to any type of beamforming being performed on the received data. Additionally, during the time period $T_2$, the channel ultrasound data from the plurality of channels 52 is processed at 36, and in particular, beamformed to generate beamformed channel data. It should be noted that the processing at 36 in various embodiments is performed concurrently or simultaneously with the receiving and storing of the channel ultrasound data. Also, it should be noted that the acquisition and storage of channel ultrasound data in various embodiments continues during a portion of all of the process 30.

The beamformer processing performed at 36 may be performed in hardware, software or a combination thereof. For example, the channel ultrasound data is processed to generate ultrasound images for display having a lower resolution or image quality, such as a basic image quality. Thus, at time period $T_3$, an image with a reduced or basic image quality is displayed at 38. For example, a lower resolution real-time image, which is a representation of the current probe image acquisition, is displayed. Thus, the processing at 36 is performed such that ultrasound images are displayed concurrently with image data acquisition such that a user is able to view the image(s) while performing an ultrasound scan. It should be noted that the beamformed channel data, namely the data that has been processed to generate the lower resolution images, also may be stored at time period $T_3$.

While the channel ultrasound data is acquired and the lower resolution image(s) are displayed, for example, while the probe is still acquiring ultrasound data and displaying lower resolution images, additional beamforming is performed on the channel data (or optionally on the beamformed channel data) at 40 (e.g., during time $T_3$) to improve the image quality. For example, additional beamforming may be performed to generate higher resolution images. Accordingly, in some embodiments a basic or lower level beamforming, which may be part of a more advanced or complex beamforming, is performed in real-time. Thus, images formed from the basic beamforming are displayed in real-time with images formed from the improved beamforming (e.g., advanced beamforming producing higher resolution images) are saved or stored, such that during, for example, a freeze operation, some or a portion of the improved beamforming is already performed.

It should be noted that the additional beamforming in various embodiments is performed in a software beamformer, which may include different types of beamforming to enhance or improve a currently displayed image or subsequently displayed images as described in more detail herein. Thus, in some embodiments, the image quality or resolution may be improved while a user is viewing real-time images (of lower resolution), replay images and/or frozen images, namely while ultrasound data is being acquired, such as during a scanning session.

It should be noted that when reference is made herein to improving image quality or resolution, this refers to any type of processing, for example, beamforming processing that changes or updates a displayed image, for example, to facilitate review or analysis of the image. An improved quality image is then displayed at 42 during time period $T_4$. The image quality or resolution may be continually improved, such that the displayed image is periodically or continually updated based on the additional beamforming processing performed during the live image acquisition mode of operation and/or a replay/freeze mode of operation (and represented by the multiple arrows 44 in FIG. 1). Accordingly, image quality of a displayed image or image cine loop may be improved, for example, during replay of an image sequence to a user. Thus, during image acquisition, a real-time processing frame rate is achieved (limited by the processing power of the system), while during replay the processed frame rate of the ultrasound system is increased above the real-time processing frame rate.

In various embodiments, the additional beamforming may be performed when a live scanning mode is terminated, for example, by a user, after a predefined or predetermined time period, at a time period when the processing power of the ultrasound system is not fully utilized or below a predetermined level, or a combination thereof. During this time period, the channel data or the beamformed channel data is further processed to change the image quality or resolution, such as to improve the image quality using one or more beamforming techniques, which may include advanced beamforming techniques. For example, one or more (or a combination thereof) of the following processing or beamforming techniques may be performed: increased multi-line acquisition (MLA), adaptive beamforming, synthetic transmit focus, aberration correction, synthetic aperture, clutter reduction and/or adaptive noise control.

Thereafter, at time period $T_5$, a final beamformed image is displayed at 46, which may include images wherein the beamforming selected by the user at $T_1$ has been completed. Additionally, the stored channel data also may be accessed to apply different beamforming techniques to that data. Accordingly, one or more images may be displayed at 48 with one or more different beamforming techniques applied thereto. The differently beamformed images may be displayed separately or concurrently on a display. Different beamforming techniques also may be performed or applied to a rendered four-dimensional (4D) image and/or to one or more two-dimensional (2D) image slices or a three-dimensional (3D) image volume.

Thus, as illustrated in FIG. 2, the ultrasound data stored in memory 50, which may be channel or processed channel data, is utilized to generate one or more ultrasound images for display. For example, a basic quality image 54 may be displayed real-time or during a live scanning mode (while ultrasound data is being acquired), which image has a lower image quality or resolution than an intermediate or finally displayed image. Additionally, one or more improved quality images 56 also may be formed, such as during a freeze mode of operation when a user is viewing a particular image, for example, additional beamforming or other processing of the ultrasound data may be performed during the freeze mode to generate images with improved beamforming (e.g., improved quality image), which may be stored for later viewing, such as after the freeze mode is terminated or has ended. An additional improved quality image 58 also may be displayed post-acquisition, for example, after the live scanning mode is terminated. The image 58 may be a finally processed, for example a finally beamformed processed image based on the selected beamforming used to generate the images 54 and/or 56, or may be an image generated using a different processing or beamforming technique post-acquisition using the channel ultrasound data.

Figure 3:
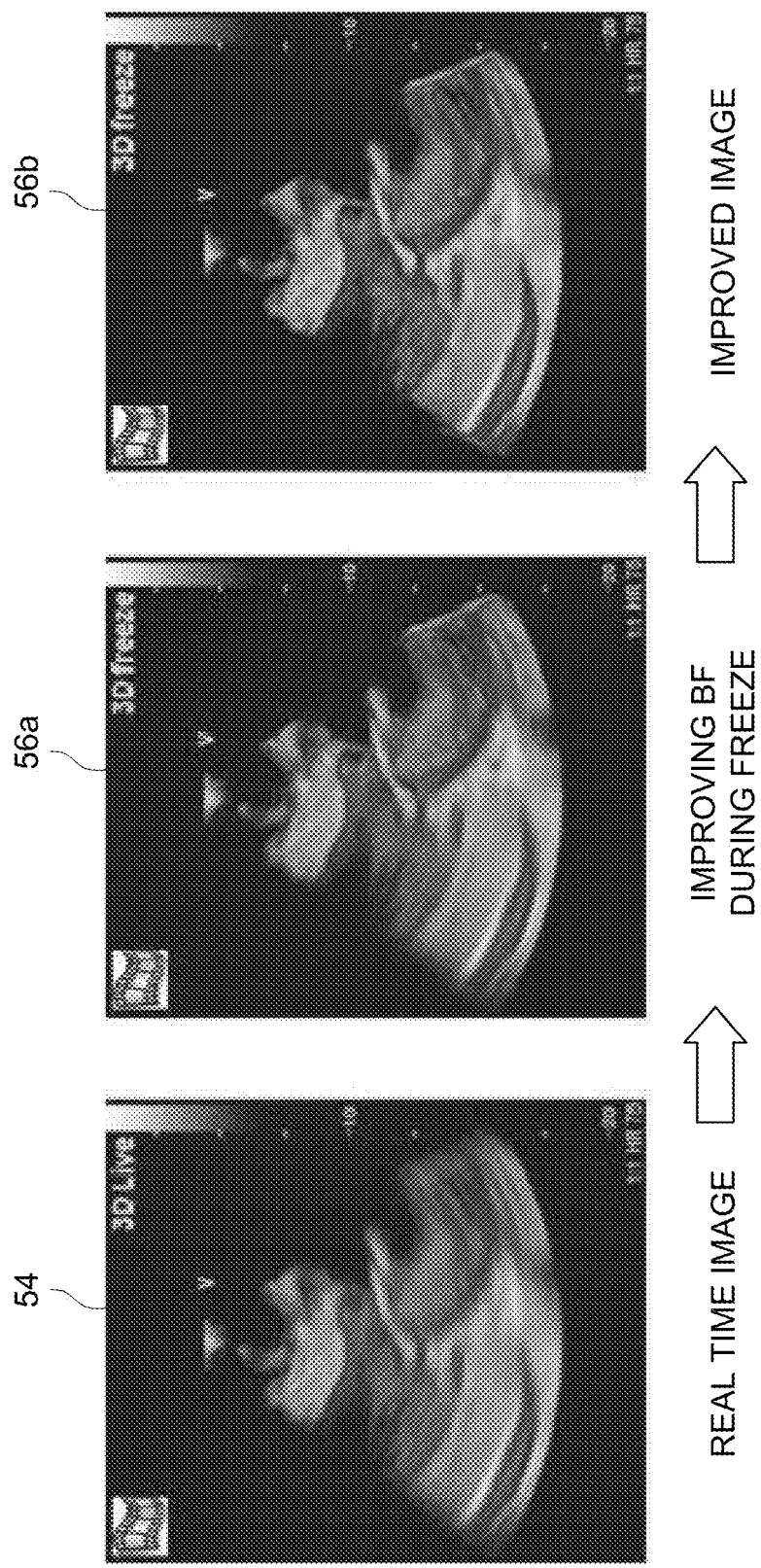
FIG. 3 is a diagram illustrating images with improved image quality or resolution generated in accordance with beamforming of various embodiments.

Thus, in operation, and as illustrated in FIG. 3, a basic quality image 54 initially may be displayed, wherein the a user is able to determine, for example, an orientation of an object and indentify larger landmarks, but the resolution is lower, such that the detailed features of the object may not be clear. It should be noted that the illustrated basic quality image 54 is a single image from a cine loop that may be displayed to a user. The image quality or resolution is then improved, which may be an incremental improvement such that updated images are displayed. For example, the improved quality image 56*a* is partly or partially improved and generated after some additional frames of image data are processed, thereby defining an updated image. The improved quality image 56*a* may have a portion of the image (e.g., half of the image) with a higher image quality or resolution. Thus, as more frames of the ultrasound data are processed, the displayed image quality or resolution improves. Accordingly, as shown in the improved quality image 56*b*, which may be the final image, the quality or resolution of the image is improved such that the detailed features of the object are clearer.

Figure 4:
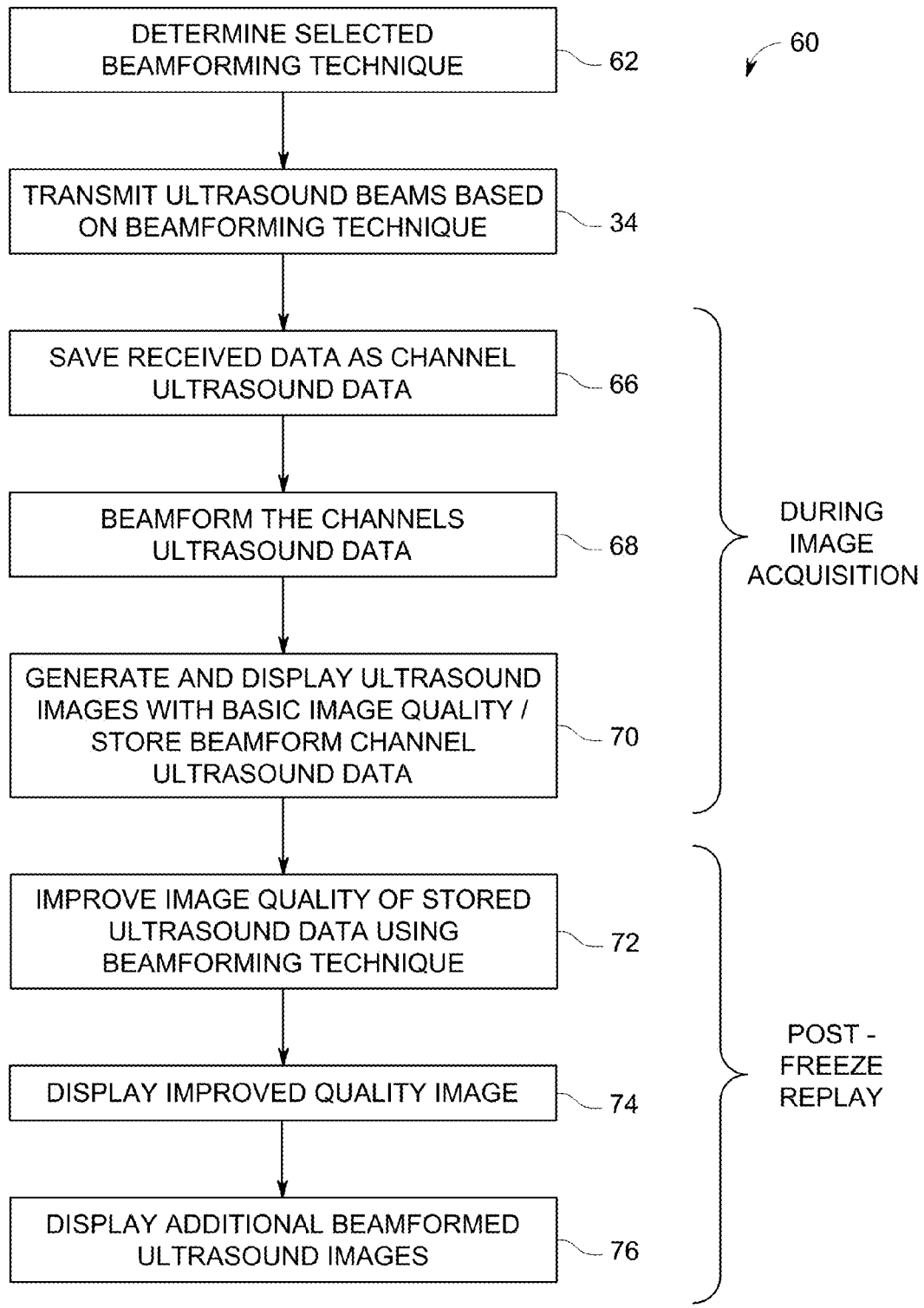
FIG. 4 is a flowchart of a method for ultrasound beamforming in accordance with various embodiments.

A method 60 for ultrasound beamforming as illustrated in FIG. 4 may be performed in accordance with various embodiments. The method 60 generally improves image quality or resolution during a scanning mode or scanning session, such as during image replay or image freeze modes. In particular, a selected beamforming technique (e.g., a beamforming method) is determined at 62. For example, a particular beamforming selected by a user to be performed on acquired ultrasound data is determined based on a user input or mode of operation.

Thereafter, ultrasound beams are transmitted at 62 based on the selected beamforming technique. For example, transmit beamforming is performed based on the selected beamforming technique to acquire ultrasound data, such as ultrasound image data of an object of interest. The received ultrasound data is saved as channel ultrasound data at 66 before receive beamforming is performed. The saved channel ultrasound data is then processed at 68, for example, to beamform the saved channel ultrasound data. It should be noted that the channel ultrasound data in various embodiments continues to be saved in a long term memory, while the beamforming processing is performed on channel ultrasound data copied to a temporary or short term memory. It also should be noted that the beamforming performed at this point, namely in real-time during a live scanning mode, provides images at a higher volume rate with lower resolution, which may include a lower line density.

The beamformed channel data is then used to generate and display at 70 ultrasound images with a basic image quality (e.g., a lower line density). The basic image, thus, has a lower image quality or resolution. The channel data is also stored, such that during an image replay or freeze, the quality or resolution of the displayed image is improved at 72 as described in more detail herein. In particular, additional beamforming is performed on the channel data using the selected beamforming technique that was partially performed to generate the images with basic image quality. For example, during a displayed cine loop of the images (e.g., a repeating cine loop of images), the quality or resolution of the images is improved, such as by processing more frames of the beamform channel data to result in images with an increased number of receive lines, or other improved image characteristics or qualities.

The improved quality images are then displayed at 74. For example, as described in more detail herein, the quality or resolution of the images may be incrementally or continually increased during repeated loops of a cine loop of images. Additionally, different types of beamforming may be performed, for example, on the saved channel ultrasound data (pre-beamformed) and also displayed at 76, which may be displayed separate from or concurrently with the improved quality images.

Thus, beamforming is performed during a live scan mode, a replay mode, a freeze mode and/or after image acquisition. For example, during a replay mode, beamforming is performed in a background operation, such that real-time background beamforming processing is provided.

In operation, and for example, in an MLA acquisition, single ultrasound beams are transmitted with multiple beams received corresponding to each transmit beam. In applications for imaging in 4D, higher frame rates are used, such as for 16 MLA and 32 MLA imaging. Ultrasound systems using various embodiments may have the processing power to produce 8 MLA, but with the beamforming of the various embodiments, can generate images at 16 MLA or 32 MLA. For example, in a 32 MLA imaging application, the various embodiments may perform 16 MLA processing during the live scanning mode and 16 MLA processing during a replay stage. Thus, about equal amounts of processing time are used during the live scanning mode and replay mode to generate higher resolution 32 MLA images. It should be noted that stored channel ultrasound data (pre-beamformed) may also be beamformed using different techniques, such as adaptive beamforming, which beamforming is performed, for example, by software beamforming.

As an example, various embodiments allow the acquisition of the whole heart volume in one heart beat, and then post-freeze a display with and improved or best achievable image quality, on an ultrasound system or scanner with reduced or limited calculation or processing power/resources. The various embodiments also allow the application of different beamforming techniques (e.g. tissue and B-Flow) on the same set of ultrasound data, without repeat scanning. It should be noted that the various embodiments are not limited to post-freeze beamforming, but also may be implemented in connection with post-freeze vector processing and image processing. For example, an advanced vector processing, such as frequency compounding uses twice the calculation or processing resources that are not available in real-time, but can be applied in post-freeze.

Figure 5:
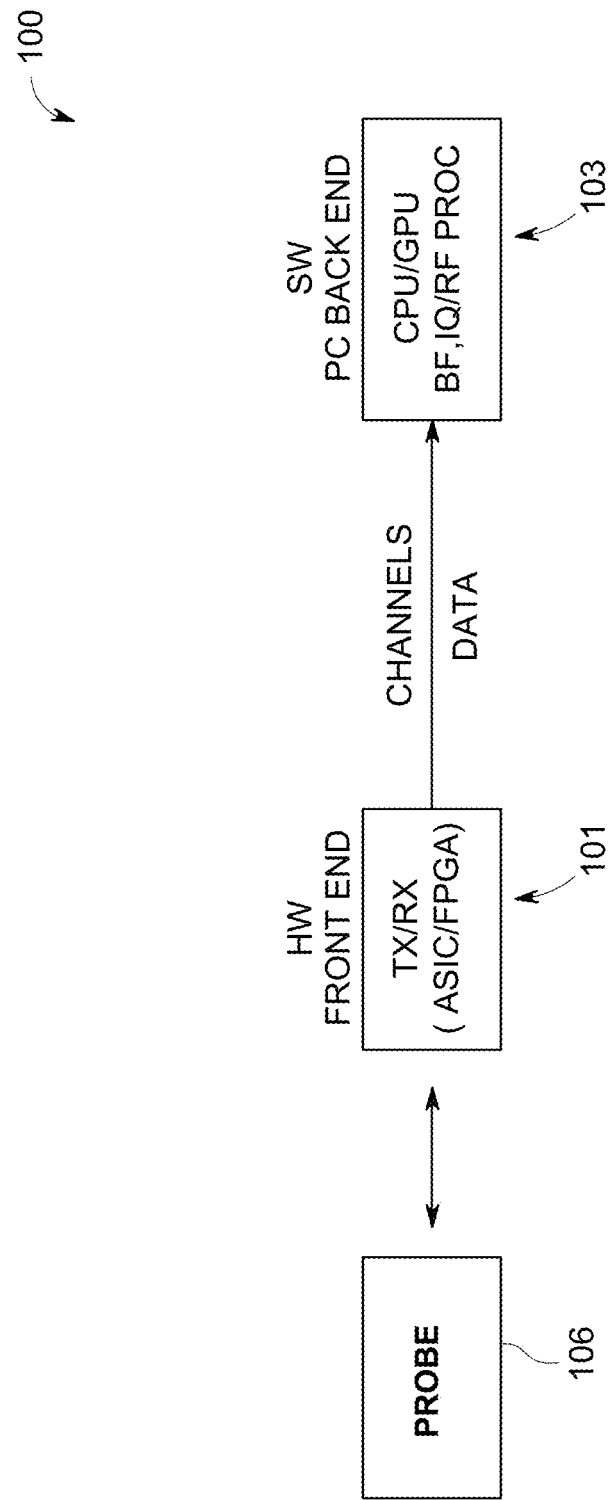
FIG. 5 is a simplified block diagram of an ultrasound system having a software beamformer for performing beamforming in accordance with various embodiments.
Figure 6:
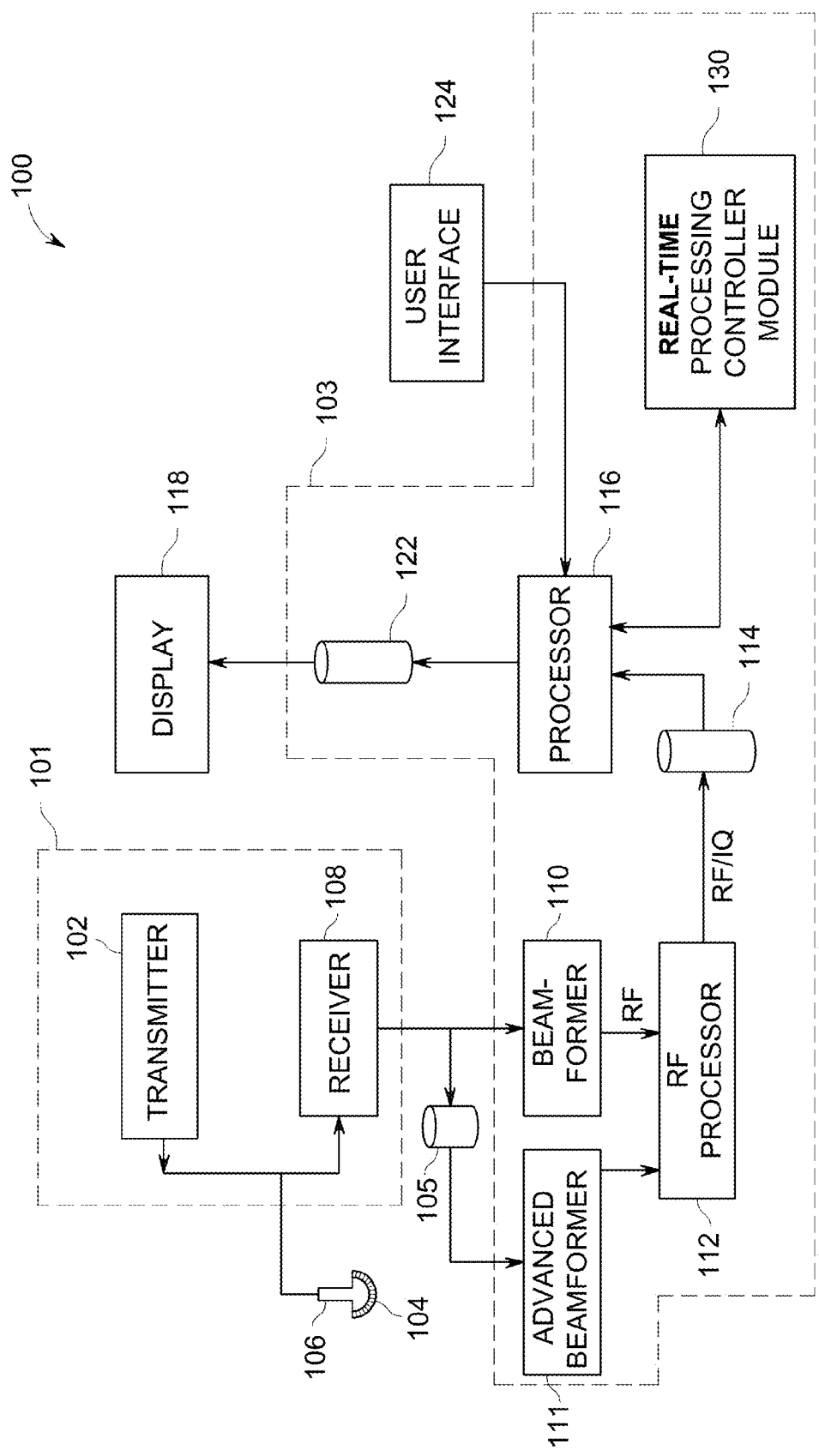
FIG. 6 is a block diagram of an ultrasound system in connection with which various embodiments may be implemented.
Figure 7:
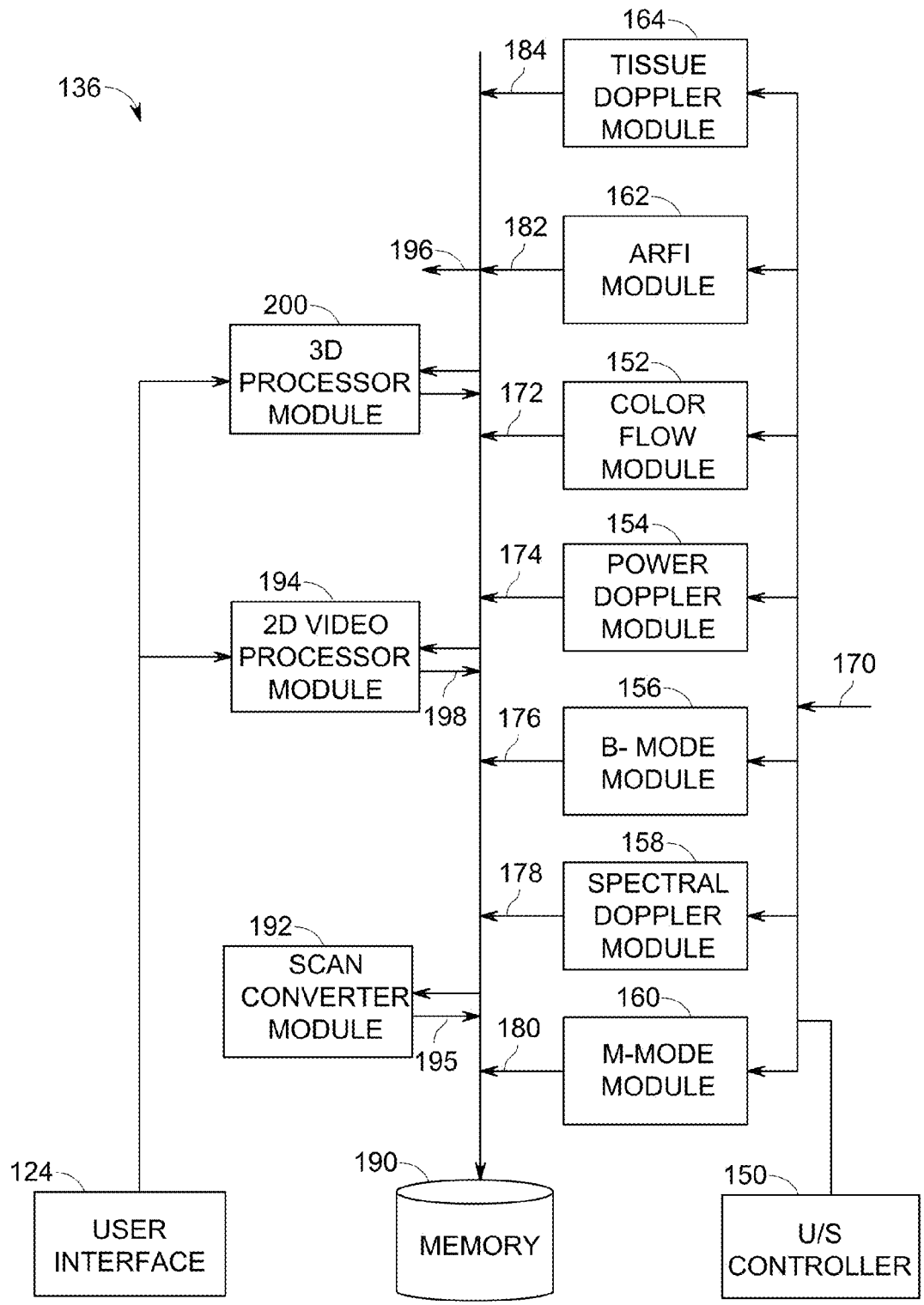
FIG. 7 is a block diagram of an ultrasound processor module of the ultrasound system of FIG. 6 formed in accordance with various embodiments.

Various embodiments may be implemented using an ultrasound imaging system 100 as illustrated in FIGS. 5 through 7. In particular, FIG. 5 is a simplified block diagram showing an ultrasound system 100 including a software beamformer architecture. The ultrasound system 100 is configured to acquire ultrasound data using a probe 106, wherein transmission and reception of ultrasound signals are provided by a front end 101, which as illustrated does not include a hardware implemented receive beamformer. However, it should be noted that a hardware implemented receive beamformer optionally may be provided to perform some beamforming as described in more detail herein. The front end 101 generally includes a transmitter/receiver, which may be implemented in, for example, an application specific integrated circuit (ASIC) or a field-programmable gate array (FPGA). The front end 101 is connected to a back end 103 via a plurality of data channels that communicate channel ultrasound data from the front end 101 to the back end 103. The back end 103 generally includes a software implemented beamformer and an IQ/RF processor as described in more detail below. These processing functions may be performed by a central processing unit (CPU), a general processing unit (GPU) or any type of programmable processor.

FIG. 6 illustrates a more detailed block diagram of the ultrasound system 100. The ultrasound system 100 is capable of electrical or mechanical steering of a soundbeam (such as in 3D space) and is configurable to acquire information corresponding to a plurality of 2D representations or images of a region of interest (ROI) in a subject or patient, which may be defined or adjusted as described in more detail herein. The ultrasound system 100 is configurable to acquire 2D images, for example, in one or more planes of orientation. The ultrasound system 100 is also capable of performing background real-time beamforming to increase the beamforming capabilities of the ultrasound system 100.

The ultrasound system 100 includes a transmitter 102 that, under the guidance of a beamformer 110, drives an array of elements 104 (e.g., piezoelectric elements) within a probe 106 to emit pulsed ultrasonic signals into a body. A variety of geometries may be used. The ultrasonic signals are back-scattered from structures in the body, like blood cells or muscular tissue, to produce echoes that return to the elements 104. The echoes are received by a receiver 108. The received echoes are saved as channel ultrasound data in a memory 105, as well as passed to a software beamformer 110, which performs receive beamforming as described in more detail herein and outputs an RF signal. It should be noted that the beamformer 110 is configured to perform basic beamforming as described herein an advanced beamformer 111 also is provided to performed advanced beamforming as described herein. The beamformers 110 and 111 may be implemented, for example, in the same software. The beamformed ultrasound data (also referred to as beamform data) also may be stored in the memory 105 or a memory 122. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage. In some embodiments a hardware receive beamformer may be provided in the front end 101.

In the above-described embodiment, the beamformer 110 operates as a receive beamformer. A transmit beamformer (not shown) is also provided. In an alternative embodiment, the probe 106 optionally includes a 2D array with subaperture receive beamforming inside the probe. The beamformer 110 may delay, apodize and sum each electrical signal with other electrical signals received from the probe 106. The summed signals represent echoes from the ultrasound beams or lines. The summed signals are output from the beamformer 110 to an RF processor 112. The RF processor 112 may generate different data types, e.g. B-mode, color Doppler (velocity/power/variance), tissue Doppler (velocity), and Doppler energy, for multiple scan planes or different scanning patterns. For example, the RF processor 112 may generate tissue Doppler data for multi-scan planes. The RF processor 112 gathers the information (e.g. I/Q, B-mode, color Doppler, tissue Doppler, and Doppler energy information) related to multiple data slices and stores the data information, which may include time stamp and orientation/rotation information, in the memory 114.

The ultrasound system 100 also includes a processor 116 to process the acquired ultrasound information (e.g., RF signal data or IQ data pairs) and prepare frames of ultrasound information for display on display 118, with the image quality or resolution improved as described in more detail herein. The processor 116 is adapted to perform one or more processing operations according to a plurality of selectable ultrasound modalities on the acquired ultrasound data. Acquired ultrasound data may be processed and displayed in real-time during a scanning session as the echo signals are received, which may include improving the image quality or resolution during a live scanning mode or replay mode controlled by a real-time processing controller module 130 that implements one or more of the various embodiments as described herein, for example, beamforming as described herein. Additionally or alternatively, the ultrasound data may be stored temporarily in memory 114 during a scanning session and then processed and displayed in an off-line operation.

The processor 116 is connected to a user interface 124 (which may include a mouser, keyboard, etc.) that may control operation of the processor 116 as explained below in more detail. A display 118 includes one or more monitors that present patient information, including diagnostic ultrasound images to the user for diagnosis and analysis. One or both of memory 114 and memory 122 may store two-dimensional (2D) or three-dimensional (3D) data sets of the ultrasound data, where such 2D and 3D data sets are accessed to present 2D (and/or 3D images), which may be in different states of beamforming. The images may be modified and the display settings of the display 118 also manually adjusted using the user interface 124.

The real-time processing controller module 130 connected to the processor 116 may be software running on the processor 116 or hardware provided as part of the processor 116. The real-time processing controller module 130 controls the software beamforming as described in more detail herein.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

FIG. 7 illustrates an exemplary block diagram of an ultrasound processor module 136, which may be embodied as the processor 116 of FIG. 6 or a portion thereof. The ultrasound processor module 136 is illustrated conceptually as a collection of sub-modules, but may be implemented utilizing any combination of dedicated hardware boards, DSPs, processors, etc. Alternatively, the sub-modules of FIG. 10 may be implemented utilizing an off-the-shelf PC with a single processor or multiple processors, with the functional operations distributed between the processors. As a further option, the sub-modules of FIG. 7 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 7 may be controlled by a local ultrasound controller 150 or by the processor module 136. The sub-modules 152-164 perform mid-processor operations. The ultrasound processor module 136 may receive ultrasound data 170 in one of several forms. In the embodiment of FIG. 6, the received ultrasound data 170 constitutes I,Q data pairs representing the real and imaginary components associated with each data sample. The I,Q data pairs are provided to one or more of a color-flow sub-module 152, a power Doppler sub-module 154, a B-mode sub-module 156, a spectral Doppler sub-module 158 and an M-mode sub-module 160. Optionally, other sub-modules may be included such as an Acoustic Radiation Force Impulse (ARFI) sub-module 162 and a Tissue Doppler (TDE) sub-module 164, among others.

Each of sub-modules 152-164 are configured to process the I,Q data pairs in a corresponding manner to generate color-flow data 172, power Doppler data 174, B-mode data 176, spectral Doppler data 178, M-mode data 180, ARFI data 182, and tissue Doppler data 184, all of which may be stored in a memory 190 (or memory 114 or memory 122 shown in FIG. 5) temporarily before subsequent processing. For example, the B-mode sub-module 156 may generate B-mode data 176 including a plurality of B-mode image planes, such as in a biplane or triplane image acquisition as described in more detail herein.

The data 172-184 may be stored, for example, as sets of vector data values, where each set defines an individual ultrasound image frame. The vector data values are generally organized based on the polar coordinate system.

A scan converter sub-module 192 accesses and obtains from the memory 190 the vector data values associated with an image frame and converts the set of vector data values to Cartesian coordinates to generate an ultrasound image frame 195 formatted for display. The ultrasound image frames 195 generated by the scan converter module 192 may be provided back to the memory 190 for subsequent processing or may be provided to the memory 114 or the memory 122.

Once the scan converter sub-module 192 generates the ultrasound image frames 195 associated with, for example, B-mode image data, and the like, the image frames may be restored in the memory 190 or communicated over a bus 196 to a database (not shown), the memory 114, the memory 122 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the channel image data to displayed grey levels. Once the video data is mapped to the grey-scale values, the display controller controls the display 118 (shown in FIG. 6), which may include one or more monitors or windows of the display, to display the image frame. The image displayed in the display 118 is produced from image frames of data in which each datum indicates the intensity or brightness of a respective pixel in the display.

Referring again to FIG. 7, a 2D video processor sub-module 194 combines one or more of the frames generated from the different types of ultrasound information. For example, the 2D video processor sub-module 194 may combine a different image frames by mapping one type of data to a grey map and mapping the other type of data to a color map for video display. In the final displayed image, color pixel data may be superimposed on the grey scale pixel data to form a single multi-mode image frame 198 (e.g., functional image) that is again re-stored in the memory 190 or communicated over the bus 196. Successive frames of images may be stored as a cine loop in the memory 190 or memory 122 (shown in FIG. 6). The cine loop represents a first in, first out circular image buffer to capture image data that is displayed to the user. The user may freeze the cine loop by entering a freeze command at the user interface 124. The user interface 124 may include, for example, a keyboard and mouse and all other input controls associated with inputting information into the ultrasound system 100 (shown in FIG. 6).

A 3D processor sub-module 200 is also controlled by the user interface 124 and accesses the memory 190 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 8:
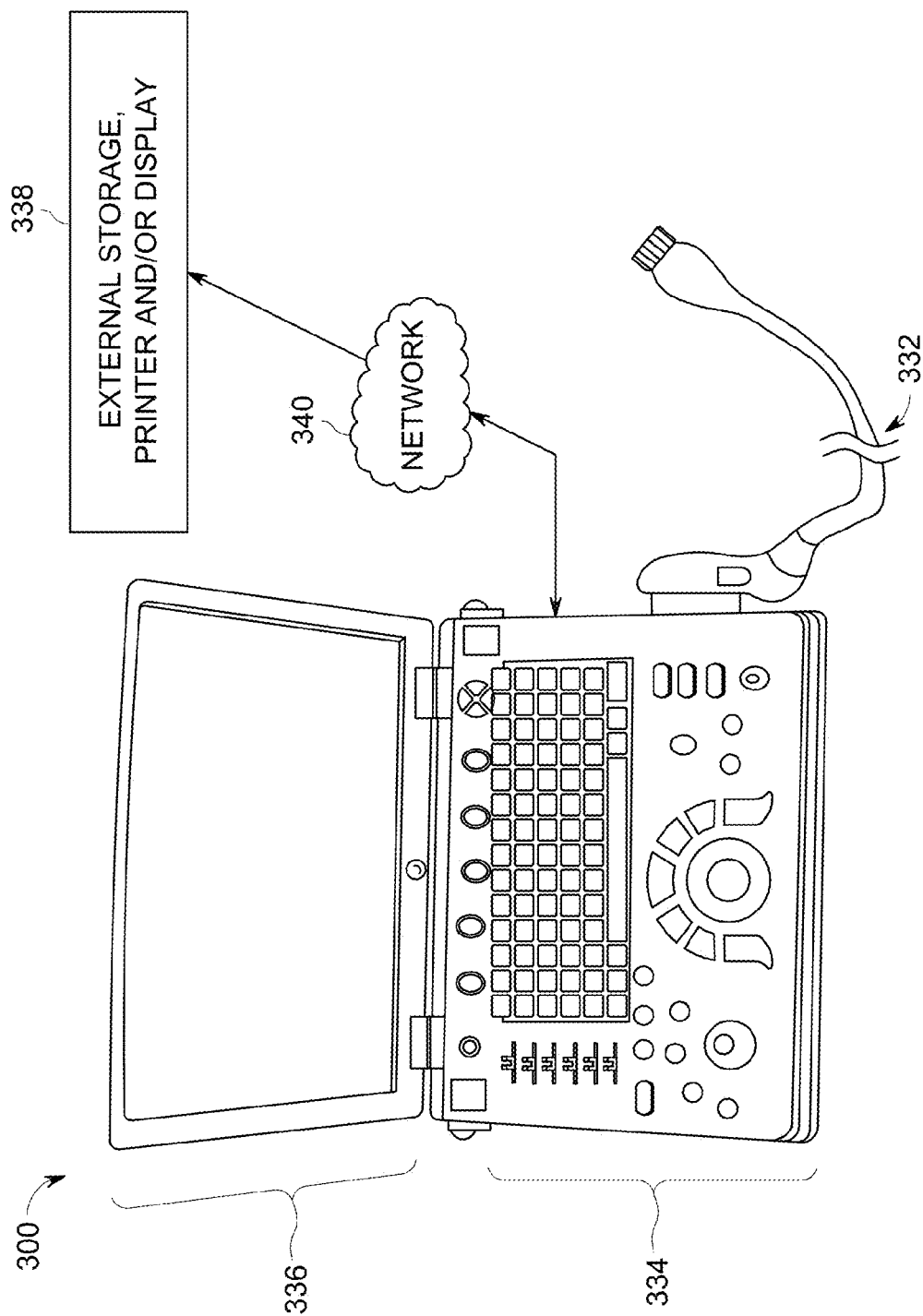
FIG. 8 is a diagram illustrating a three-dimensional (3D) capable miniaturized ultrasound system in which various embodiments may be implemented.
Figure 9:
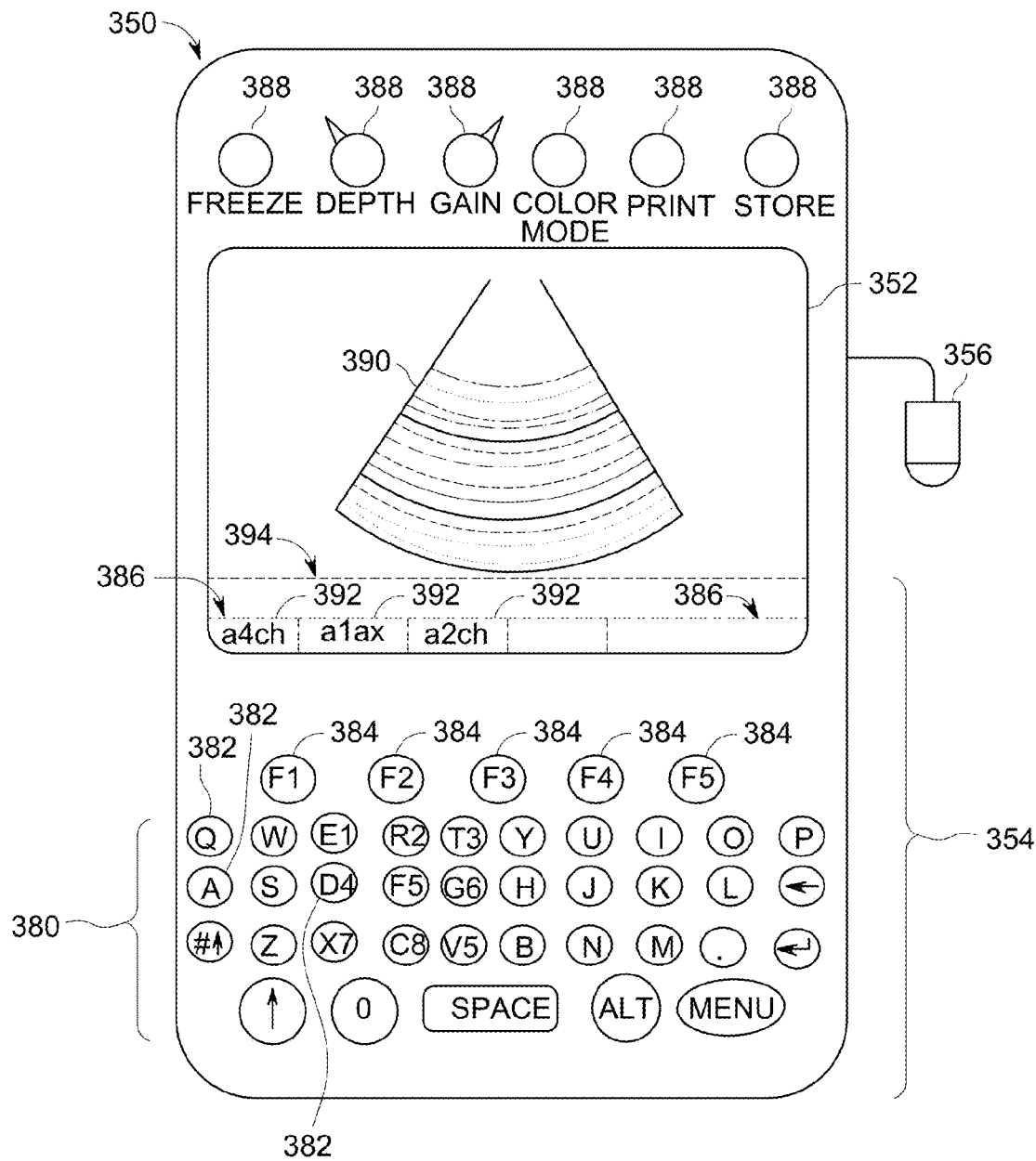
FIG. 9 is a diagram illustrating a 3D capable hand carried or pocket-sized ultrasound imaging system in which various embodiments may be implemented.
Figure 10:
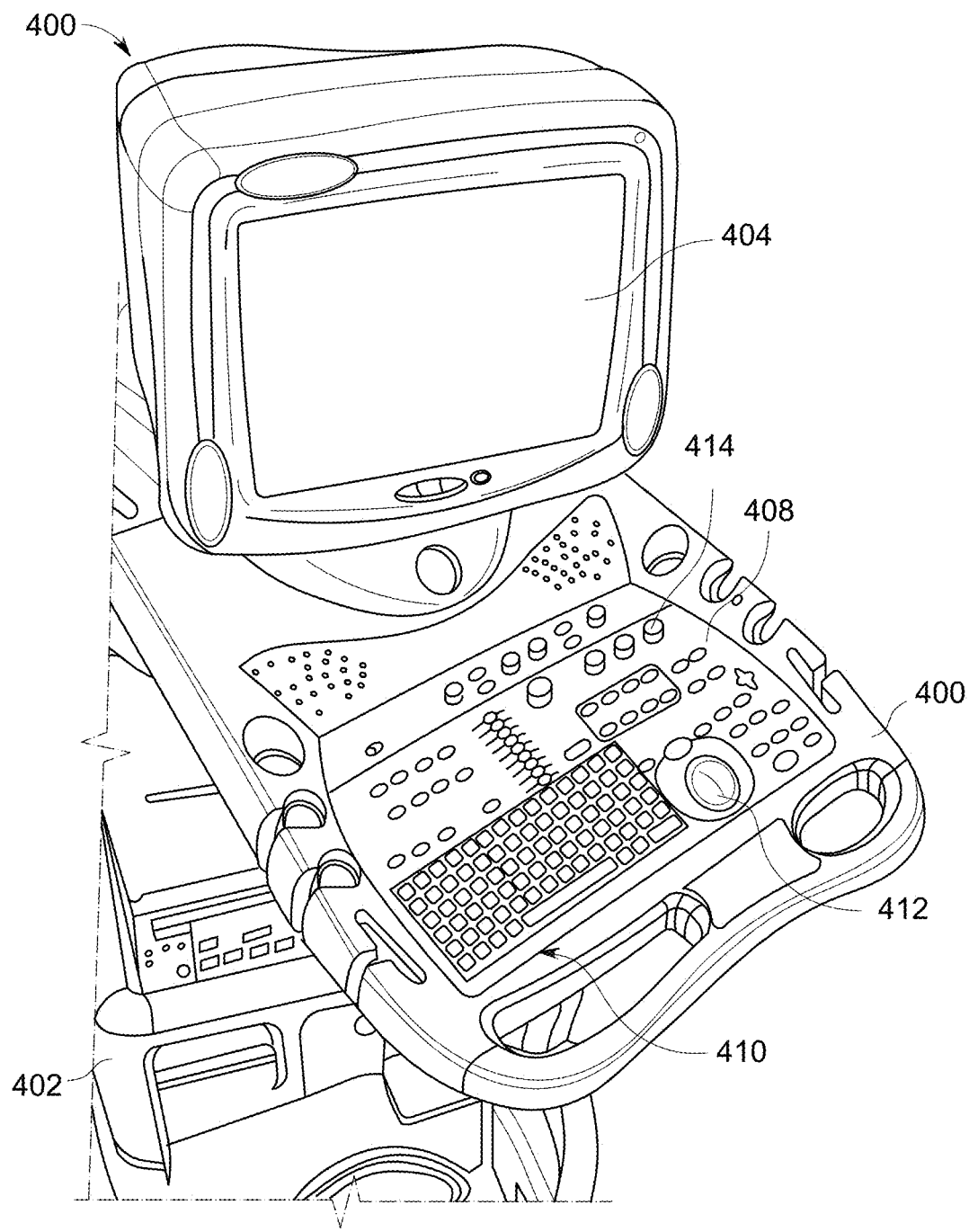
FIG. 10 is a diagram illustrating a 3D capable console type ultrasound imaging system in which various embodiments may be implemented.

The ultrasound system 100 of FIG. 6 may be embodied in a small-sized system, such as laptop computer or pocket sized system as well as in a larger console-type system. FIGS. 8 and 9 illustrate small-sized systems, while FIG. 10 illustrates a larger system.

FIG. 8 illustrates a 3D-capable miniaturized ultrasound system 300 having a probe 332 that may be configured to acquire 3D ultrasonic data or multi-plane ultrasonic data. For example, the probe 332 may have a 2D array of elements 104 as discussed previously with respect to the probe 106 of FIG. 6. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 9 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 100 (shown in FIG. 6)

FIG. 10 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that the various embodiments may be implemented in hardware, software or a combination thereof. The various embodiments and/or components, for example, the modules, or components and controllers therein, also may be implemented as part of one or more computers or processors. The various embodiments and/or components may be implemented in a different order or arrangement. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for forming images from ultrasound data, the method comprising:
    acquiring channel ultrasound data from a plurality of channels connected to a plurality of elements of an ultrasound probe;
    storing the channel ultrasound data from the plurality of channels;
    generating first ultrasound images by processing the stored channel ultrasound data, wherein the processing comprises of performing partial beamforming of at least some of the stored channel ultrasound data;
    displaying the first ultrasound images during acquisition of the channel ultrasound data;
    performing additional processing on the stored channel ultrasound data while the first ultrasound images are displayed during an image freeze mode; and
    generating and displaying updated ultrasound images generated by the additional processing, the updated ultrasound images having a higher image quality or resolution as compared to the first ultrasound images displayed before performing the additional processing, wherein the additional processing comprises of at least performing additional beamforming on the partially beamformed stored channel ultrasound data that was used to generate the first ultrasound images.

2. A method in accordance with claim 1 wherein the first ultrasound images comprise images having a basic image quality that is lower than higher image quality or resolution.

3. A method in accordance with claim 1 wherein the stored channel ultrasound data comprises a plurality of image frames and generating the first ultrasound images comprises processing a portion of the plurality of image frames, and performing the additional processing comprises processing additional frames of the plurality of image frames not previously processed and further comprising displaying incrementally updated ultrasound images based on the additional processing performed using the additional image frames.

4. A method in accordance with claim 1 wherein the image freeze mode is performed during a replay mode of operation and further comprising performing the processing to generate the first ultrasound images during a live scanning mode, and performing the additional processing during the replay mode of operation while acquiring additional channel ultrasound data.

5. A method in accordance with claim 1 further comprising storing the acquired channel ultrasound data in a long term memory while processing the acquired channel ultrasound data copied to a short term memory, and further performing a different type of processing on the channel ultrasound data stored in the long term memory.

6. A method in accordance with claim 1 wherein the additional processing is further performed during display of cine images.

7. A method in accordance with claim 1 wherein the processing of the stored channel ultrasound data to generate the first images comprises hardware processing and the additional processing comprises software processing.

8. A method in accordance with claim 1 wherein the processing of the stored channel ultrasound data to generate the first ultrasound images comprises software processing and the additional processing comprises software processing.

9. A method in accordance with claim 1 wherein the additional processing comprises processing operations exceeding a real-time processing capability of an ultrasound system.

10. A method in accordance with claim 1 wherein the processing to generate the first ultrasound images comprises a basic beamforming technique that is less advanced that an advanced beamforming technique, and the additional processing comprises the advanced beamforming technique allowing generation of the updated ultrasound images having the higher image quality or resolution.

11. A method in accordance with claim 1 wherein the additional processing is performed when a processing utilization of an ultrasound system is below a predetermined level.

12. A method in accordance with claim 1 wherein the displaying updated ultrasound images comprises generating the updated ultrasound images through the additional processing of the stored ultrasound data, wherein the updated ultrasound images relate to the stored ultrasound data.

13. A method for forming images from ultrasound data, the method comprising:
acquiring channel ultrasound data from a plurality of channels connected to a plurality of elements of an ultrasound probe;
storing the channel ultrasound data from the plurality of channels;
forming a pixel image from the stored channel ultrasound data, wherein the pixel image is formed by performing partial beamforming of at least some of the stored channel ultrasound data;
displaying the pixel image;
performing additional processing on the stored channel ultrasound data while the pixel image is displayed during an image freeze mode;
generating an updated ultrasound image by performing the additional processing, the additional processing comprising additional beamforming on the partially beamformed stored channel ultrasound data; and
displaying the updated ultrasound image, wherein the updated ultrasound image has a higher image quality or resolution as compared to the pixel image.

14. A method in accordance with claim 13 wherein the displaying an updated ultrasound image comprises generating the updated ultrasound image through the additional processing of the stored channel ultrasound data, wherein the updated ultrasound image relates to the stored ultrasound channel data.

* * * * *